United States Patent
Kropp et al.

(10) Patent No.: US 8,433,110 B2
(45) Date of Patent: Apr. 30, 2013

(54) PULSE-RATE DETECTION USING A FINGERPRINT SENSOR

(75) Inventors: Ronald A. Kropp, West Palm Beach, FL (US); Richard Irving, Palm Beach Gardens, FL (US); Rainer M. Schmitt, Palm Beach Gardens, FL (US)

(73) Assignee: Sonavation, Inc., Palm Beach Gardens, FL (US)

( * ) Notice: Subject to any disclaimer, the term of this patent is extended or adjusted under 35 U.S.C. 154(b) by 307 days.

(21) Appl. No.: 12/966,328

(22) Filed: Dec. 13, 2010

(65) Prior Publication Data

US 2011/0170750 A1    Jul. 14, 2011

Related U.S. Application Data

(60) Provisional application No. 61/285,793, filed on Dec. 11, 2009.

(51) Int. Cl.
*G06K 9/00*    (2006.01)
(52) U.S. Cl.
USPC .......................................................... 382/124
(58) Field of Classification Search .................. None
See application file for complete search history.

(56) References Cited

U.S. PATENT DOCUMENTS

| 5,978,495 | A | 11/1999 | Thomopoulos et al. |
| 6,459,804 | B2 * | 10/2002 | Mainguet ...................... 382/124 |
| 6,885,439 | B2 * | 4/2005 | Fujieda ........................... 356/71 |
| 2006/0204062 | A1 | 9/2006 | Shigeta |
| 2007/0177772 | A1 * | 8/2007 | Fujii et al. ...................... 382/115 |
| 2008/0273768 | A1 | 11/2008 | Dennis et al. |
| 2009/0069668 | A1 | 3/2009 | Stemmer |
| 2009/0092290 | A1 | 4/2009 | Rowe |

OTHER PUBLICATIONS

Search Report and Written Opinion for International Application No. PCT/US10/60073 mailed Feb. 11, 2011, 17 pages.

* cited by examiner

*Primary Examiner* — Stephen R Koziol
*Assistant Examiner* — Raphael Schwartz
(74) *Attorney, Agent, or Firm* — Kenneth J. Lukacher Law Group

(57) ABSTRACT

Provided is a fingerprint sensor configured for detecting a pulse of a human or other mammal. A time series of fingerprint images is analyzed to identify time-based variations in spatial location and/or pressure from ridges of a finger, where the variations result from time-based variations in the flow of blood. Based on the analysis, a determination is made if the time-based variations are indicative of a pulse in a digit of the person, and if so, a determination is made as to the pulse rate based on the variations. Imaging sensitivity of the digit at the fingerprint sensor is optimized for determination of the pulse. The time series of fingerprint images is also analyzed to determine if there is bulk motion of the digit, in which case pulse rate analysis is temporarily suspended.

30 Claims, 10 Drawing Sheets

Fingerprint Ridges at low pulse (diastole)

Fingerprint Ridges at low pulse (diastole)

Fingerprint Ridges at high pulse (systole)

Fingerprint Ridges at low pulse (diastole)

Fingerprint Ridges at high pulse (systole)

Exemplary Platen With Sensing Matrix

Exemplary Method For Detecting
A Pulse With Fingerprint Sensor

Exemplary Method To Process Pressure/location
Fluctuations To Determine Instantaneous
Fluctuation Intensity For Each Time Slice

PULSE-RATE DETECTION USING A FINGERPRINT SENSOR

CROSS-REFERENCE TO RELATED APPLICATIONS

This application claims benefit to U.S. Provisional Application No. 61/285,793 filed on Dec. 11, 2009, which is incorporated by reference herein in its entirety.

BACKGROUND OF THE INVENTION

1. Field of the Invention

The present invention generally relates to biometrics.

2. Background Art

A variety of well known techniques exist for sensing, measuring, and identifying biometric characteristics. These techniques focus on unique characteristics associated with structures that form the biometrics, and which can therefore uniquely identify an individual. By way of one example, fingerprints, defined by ridges and valleys in a finger, are one such biometric.

Similarly, a variety of techniques exist for sensing and measuring physiological functions. For example, a pulse rate, defined as the number of beats-per-minute of the heart, is a measurable physiological function.

Typically, the sensors used to measure biometric information are different in structure and function from those used to measure physiological activities. For example, the optical imaging, capacitive, and piezoelectric devices typically used to detect fingerprints are quite different in structure, design and operation from the plethysmographic or infrared devices used to measure a pulse.

In some instances, however, it may be convenient or useful to obtain both biometric information and physiological activity data via a single sensor. For example, in a fingerprint sensor, it may be useful both to form an image of a fingerprint, and also to determine that the fingerprint is actually from a live finger. Therefore, combining both fingerprint detection and pulse detection in a single device may be of practical benefit for security purposes.

In other cases, such a combination may prove convenient. For example, a person carrying a personal digital support device, a medical device, or a communication device may wish to identify themselves to the device via biometric identification. At other times, the same person may also wish to use the device to monitor a physiological parameter such as pulse, for example for medical monitoring purposes.

What is needed, therefore, are systems and methods that enable pulse detection in devices conventionally configured for fingerprint detection.

BRIEF SUMMARY OF THE INVENTION

In one embodiment, the present invention includes a fingerprint sensor, which may be a standalone fingerprint sensor or a fingerprint sensor coupled with or integrated into another technology (for example, a cell phone or a computer). The fingerprint sensor includes a biometric sensing element for the fingerprint detection, and can include, or be coupled to, a processor. The system of fingerprint sensor and processor may also contain, or be coupled to, a memory configured to store image data and/or to store instructions for processing image data.

The biometric sensing element is configured to obtain, and to send to the processor and/or memory, a time series of images of at least a portion of a fingerprint. Using the processor, earlier and later images from the time series of images of the fingerprint are compared. Differences in the time series of images are identified.

The present invention determines whether the differences in images are so large as to be the result of bulk motion of a finger or other digit in relation to the biometric sensor, in which case the images are not used to obtain heart rate data. If, in bulk aspect, the digit is substantially stationary relative to the biometric sensor, then smaller, more subtle changes in the fingerprint over time are detected. These changes in the fingerprint are induced by the pulse of blood through the digit, and may be either small changes in the pressure of ridges from the digit, or small changes in the spatial location of the ridges relative to pixels or coordinate locations on the biometric sensor, or both.

The changes in the fingerprint are analyzed to determine a substantially cyclical pattern which is substantially stable over a short period of time (for example, over several seconds), and which falls within a typical range for a pulse. Such a substantially cyclical pattern of the change in the fingerprint, within an acceptable range and of acceptable stability, is identified as being a result of the pulse. The identified pulse may then be displayed to a user, stored in data storage, transmitted, etc.

Additional features and advantages of the invention will be set forth in the description that follows, and in part will be apparent from the description, or may be learned by practice of the invention. The advantages of the invention will be realized and attained by the structure and particularly pointed out in the written description and claims hereof, as well as the appended drawings.

It is to be understood that both the foregoing general description and the following detailed description are exemplary and explanatory and are intended to provide further explanation of the invention as claimed.

BRIEF DESCRIPTION OF THE DRAWINGS/FIGURES

The accompanying drawings illustrate the present invention and, together with the description, further serve to explain the principles of the invention and to enable one skilled in the pertinent art to make and use the invention. In the drawings, like reference numbers indicate identical or functionally similar elements. Additionally, the left most digit or digits of a reference number identifies the drawing in which the reference number first appears. Additionally, some elements may be identified or further identified by a reference number followed by a letter of the alphabet, for example "110a," "110b." In these cases the number by itself (e.g., "110") may identify a generic class or generic instance of an element, while the letter of the alphabet ("a," "b," etc.) may identify a more specific instance or embodiment of the element. In some cases only specific instances or embodiments are illustrated (e.g., "102a," "102b," "102c," etc.), it being understood that the number when used by itself (e.g., "102") may refer to either a single or multiple specific instances, depending on the context.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the invention. Therefore, the following detailed description is not meant to limit the invention. Rather, the scope of the invention is defined by the appended claims.

It will be apparent to one skilled in the art that the present invention, as described below, may be implemented in many different embodiments. Any actual software code implementing the present invention is not limiting of the present invention. Thus, the operational behavior of the present invention will be described with the understanding that modifications and variations of the embodiments are possible, given the level of detail presented herein.

Exemplary Fingerprints and Fingerprint Sensors

As known to those of skill in the art, fingerprints are defined by unique structures on the surface of the finger called ridges and valleys.

Figure 1A:
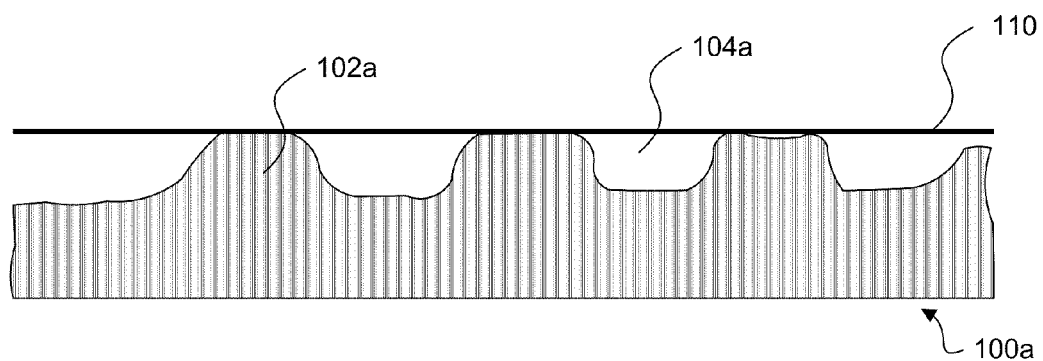
FIG. 1A is an illustration of an exemplary fingerprint during a period of diastolic pressure (low pressure).
Figure 1B:
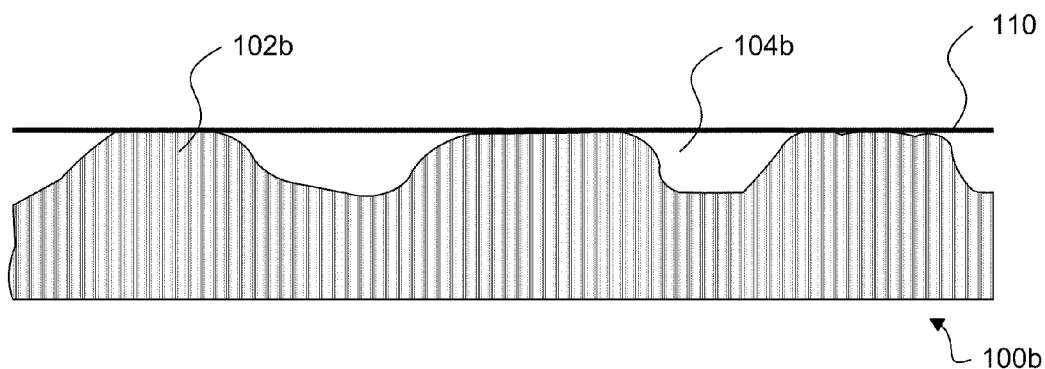
FIG. 1B is an illustration of the exemplary fingerprint of FIG. 1A during a period of systolic pressure (high pressure).

FIGS. 1A and 1B are illustrations of the basic structure 100 of a fingerprint (illustrated in two views as 100a and 100b). In FIGS. 1A and 1B, the basic fingerprint structure 100 includes ridges 102 and valleys 104 (illustrated as ridges 102a, 102b and valleys 104a, 104b, respectively), which combine to form an entire fingerprint (elements 106a, 106b of FIGS. 1C and 1D, discussed below). Ridges 102 are fingerprint tissue, while valleys 104 are regions or empty space (or, typically air) between the ridges.

As will be discussed further below, in one embodiment the invention is directed towards a system and method for detecting the pulse of a mammal, such as a person, using a sensor which is conventionally configured as a fingerprint sensor.

In FIGS. 1A and 1B, fingerprint structure 100 is shown pressed against a platen 110 (i.e. a sensing surface of a fingerprint sensor). Exemplary fingerprint sensors, including platen 110, are described in further detail below in conjunctions with FIGS. 2A, 2B, 3, and 4.

Figure 1C:
FIG. 1C is an illustration of another exemplary fingerprint during a period of diastolic pressure (low pressure).
Figure 1D:
FIG. 1D is an illustration of the exemplary fingerprint of FIG. 1C during a period of systolic pressure (high pressure).

FIGS. 1C and 1D illustrate a complete fingerprint 106 of a digit of a mammal (illustrated in two views as fingerprints 106a and 106b).

FIG. 1A is distinguished from FIG. 1B in that FIG. 1A represents the fingerprint tissue during an interval of diastolic pressure (low blood pressure) when the heart is at rest during a cardiac cycle. FIG. 1B represents the fingerprint tissue during an interval of systolic pressure (high blood pressure) when the heart is pumping blood at maximum pressure during a cardiac cycle. Similarly, FIGS. 1C and 1D are distinguished by representing the fingerprint during diastolic pressure and systolic pressure, respectively.

The present invention is based on variations in the fingerprint between the diastolic and systolic points of the cardiac cycle. During the diastolic interval or low blood pressure interval, the ridges 102 of fingerprint 106 will be closer together, and fingerprint 106 will exert less pressure on platen 110. During an interval of systolic pressure or high blood pressure, the ridges 102 of fingerprint 106 will expand further from each other and ridges 102 will place higher pressure and be broader in their signature against platen 110.

FIG. 1A compared to FIG. 1B illustrates the difference in the fingerprint structure 100 between the diastolic and systolic intervals of a cardiac cycle. Similarly, FIGS. 1C and 1D illustrates the change in the fingerprint 106 between the diastolic and systolic intervals of the cardiac cycle. In each case, the area of contact between the ridges 102 and platen 110 may be increased during the systole as compared to the diastole, and the fingerprint structure 100 or fingerprint as a whole 106 may be distended during systole as compared with diastole.

It should be noted that for purposes of illustration, the differences in fingerprint structure 100 between the diastolic interval and the systolic interval have been artificially exaggerated in FIG. 1A as compared to FIG. 1B. Similarly, the differences in fingerprint 106 have been greatly exaggerated between FIG. 1C and FIG. 1D. Persons skilled in the relevant art will recognize that the system and method disclosed herein will be capable of distinguishing much smaller, more subtle variations in the fingerprint between the diastolic and systolic intervals, which may be detected by the fingerprint sensor.

The ridges 102 and valleys 104 of fingerprint 106 can be sensed, measured, and identified based upon a number of different modalities. These modalities sense differences between the fingerprint ridges and valleys with respect to dielectric permittivity, thermal conductivity, acoustic impedance, optical index, or other sensing modalities.

For example, some fingerprint measurement modalities rely on density values associated with the ridges and valleys. Acoustic impediography, employing for example piezoelectric sensing elements, is one means to distinguish the density variations between ridges and valleys.

Other modalities rely on dielectric permittivity as measured when an electric current is passed through the ridges and valleys. With respect to dielectric permittivity for example, the permittivity of a ridge (i.e., tissue), is different from the permittivity of a valley (i.e., air between the ridges). Capacitive sensing is one technique that can be used to detect changes in permittivity. With capacitive sensing, capacitance values generated when a sensor plate (electrode) touches a ridge are different than those generated when the sensor is exposed to a valley.

Yet another modality is thermal conductance which is a measure of the temperature differences between the ridges and valleys. Optics are yet another modality. Optical techniques rely on an optical index of refractive and reflective changes between the ridges and the valleys.

Although the modalities differ, each approach seeks to accurately distinguish ridges from valleys in order to image the fingerprint or otherwise capture an impression of the fingerprint. An "impression of a fingerprint" is any data which may be captured by platen 110, and which is descriptive of or otherwise captures or is indicative of the structure of the fingerprint, which may include the shape of the fingerprint (as defined by the ridges and valleys), the pressure exerted by the fingerprint, and/or other structural aspects of the fingerprint. Such data may include, for example and without limitation, fingerprint image data, fingerprint pressure data, dielectric permittivity data associated with the fingerprint, capacitive data associated with the fingerprint, thermal conductance data associated with the fingerprint, and/or optical index data associated with the fingerprint.

Figure 2A:
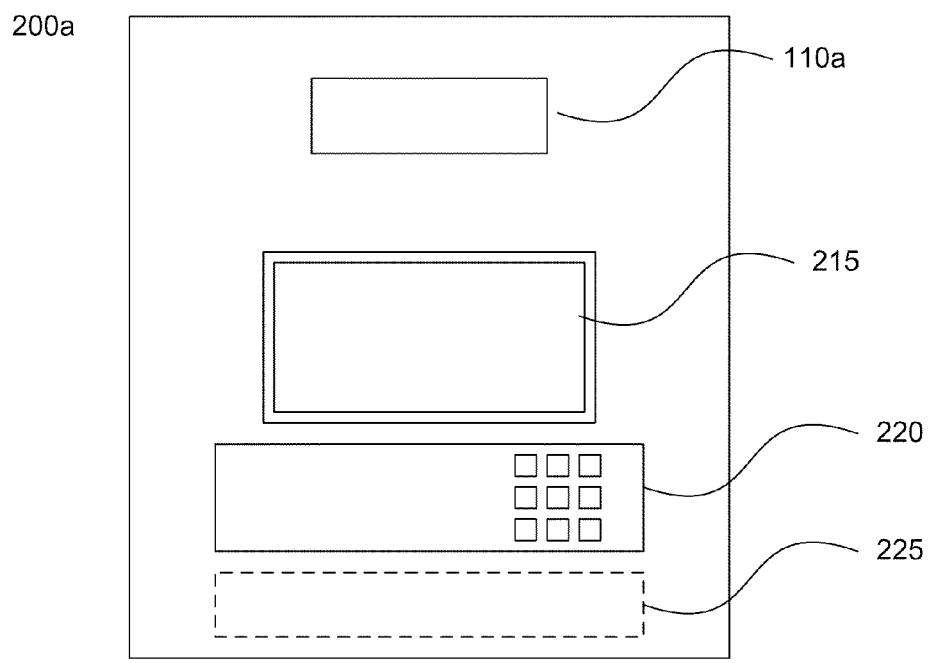
FIG. 2A is an illustration of an exemplary fingerprint sensor.

FIG. 2A illustrates an exemplary fingerprint sensor 200a. It should be noted that exemplary fingerprint sensor 200a may be a standalone fingerprint sensor, or can be combined with or integrated into another electronic device. For example, fingerprint sensor 200a can be part of a portable communications device such as a cell phone or personal digital assistant. Fingerprint sensor 200a can also be part of a personal computer or laptop computer. In these configurations, elements of fingerprint sensor 200a can serve additional purposes other than those specifically indicated herein. For example, a display element 215, discussed further below, can provide display functions not only for fingerprint sensor 200a, but for the cell phone, personal digital assistant, laptop computer, or other similar device. Fingerprint sensor 200a can be integrated into these other devices, in part or in whole because fingerprint sensor 200a can serve to provide biometric identification and security for the device.

Fingerprint sensor 200a includes platen or sensor pad 110a (discussed above in conjunction with FIG. 1), a display 215, a control panel 220, and a processing system 225.

Platen 110a can also be referred to as a sensor pad, a sensor plate, or as a biometric sensing element. Platen 110a is configured to receive a digit of a person or other mammal, such as a finger of a person. Platen 110a is configured with sensing elements, discussed further below, which are capable of detecting distinguishing elements of fingerprint 106. In an embodiment, platen 110a is configured to detect ridges 102 and valleys 104 of fingerprint 106. The platen 110a is sufficiently wide to receive a full width of fingerprint 106, but can be narrow enough in height to only receive a portion of a vertical section of fingerprint 106. Therefore, fingerprint sensor 110a can require that to detect fingerprint 106, a user must swipe or scroll their finger across platen 110a.

In an embodiment illustrated in FIG. 1, platen 110a is configured to return an image of fingerprint 106 consisting of pixel elements as discussed further below in conjunction with FIG. 3. Platen 110a is also configured to return a time series of images of fingerprint 106. In alternative embodiments, platen 110a can be configured to return data other than image data which is descriptive of the structure of fingerprint 106. Such data may be in alternative to, or in addition to, image data of fingerprint 106. As noted above, the data captured by platen 110a and which is descriptive of the structure 100 of fingerprint 106 is generically referred to as an impression of fingerprint 106.

Sensor 200a includes display element 215. Display element 215 can be used to display a variety of information pertinent to the use of fingerprint sensor 200a. For example, display 215 can display instructions for the use of fingerprint sensor 200a. Display 215 can also display a result of a fingerprint detection, for example, a biometric determination of a user. Control panel 220 can include a variety of controls used by fingerprint sensor 200a. For example, control panel 220 can include controls to initiate a scan of a fingerprint, and can include controls to initiate a pulse detection using fingerprint scanner 200a.

Fingerprint sensor 200a also includes a processing system 225, shown in FIG. 2A with a dotted outline. The dotted line indicates that processing system 225 is typically internal to fingerprint sensor 200a. Processing system 225 includes a variety of elements necessary to process fingerprint scanning information, and also to detect and process a cardiac pulse. The details of processing system 225 are discussed below in greater detail in conjunction with FIG. 4. As will be discussed in detail below, processing system 225 is configured to detect a variation over time of fingerprint 106, or in a portion of a fingerprint 106, returned by platen 110. In particular, and as will also be discussed in further detail below, processing system 225 is configured to detect the variation over time in fingerprint 106 by comparing images or other fingerprint impressions from a time series of images, or time series of impressions, returned by platen 110.

Figure 2B:
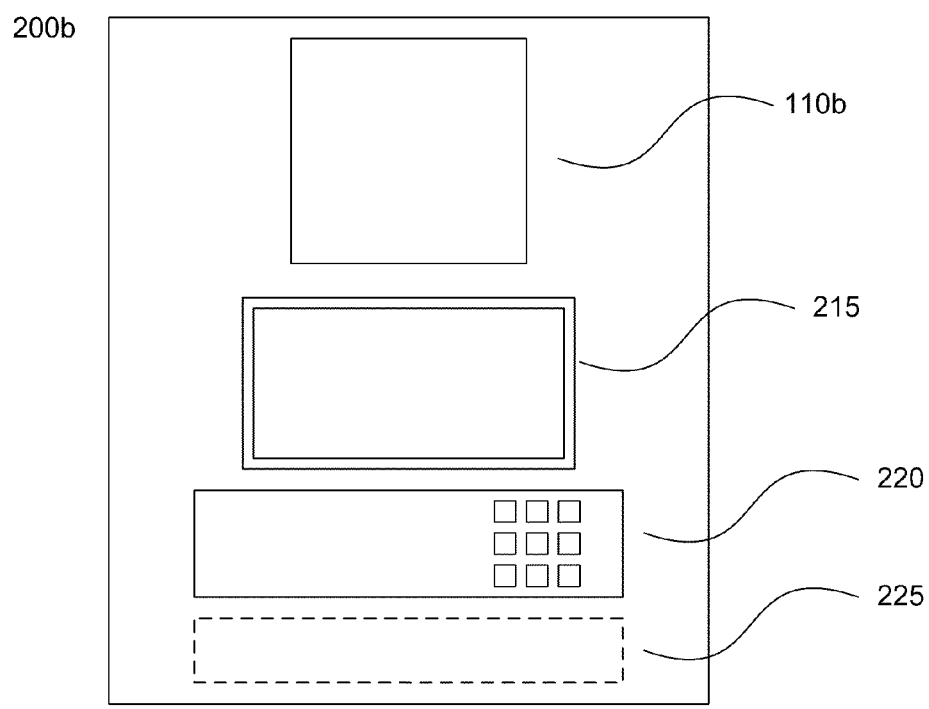
FIG. 2B is an illustration of another exemplary fingerprint sensor.

FIG. 2B is a view of another exemplary fingerprint sensor 200b. Most of the elements of exemplary fingerprint sensor 200b are the same as elements of exemplary fingerprint sensor 200a discussed above, and the details of these elements will not be repeated here. One distinguishing feature between fingerprint sensor 200b and 200a is a sensor platen 110b. Sensor platen 110b is configured to be both tall enough and wide enough to receive an entire fingerprint. Therefore, in conjunction with sensor 200b and platen 110b, a user would not be required to move or swipe their finger across platen 110b.

It should be noted that exemplary fingerprint sensors 200a and 200b may include other elements not specifically illustrated or discussed, such as for example power elements, various ports for communications with other technologies (and which may serve as additional control elements), and other elements as well.

Figure 3:
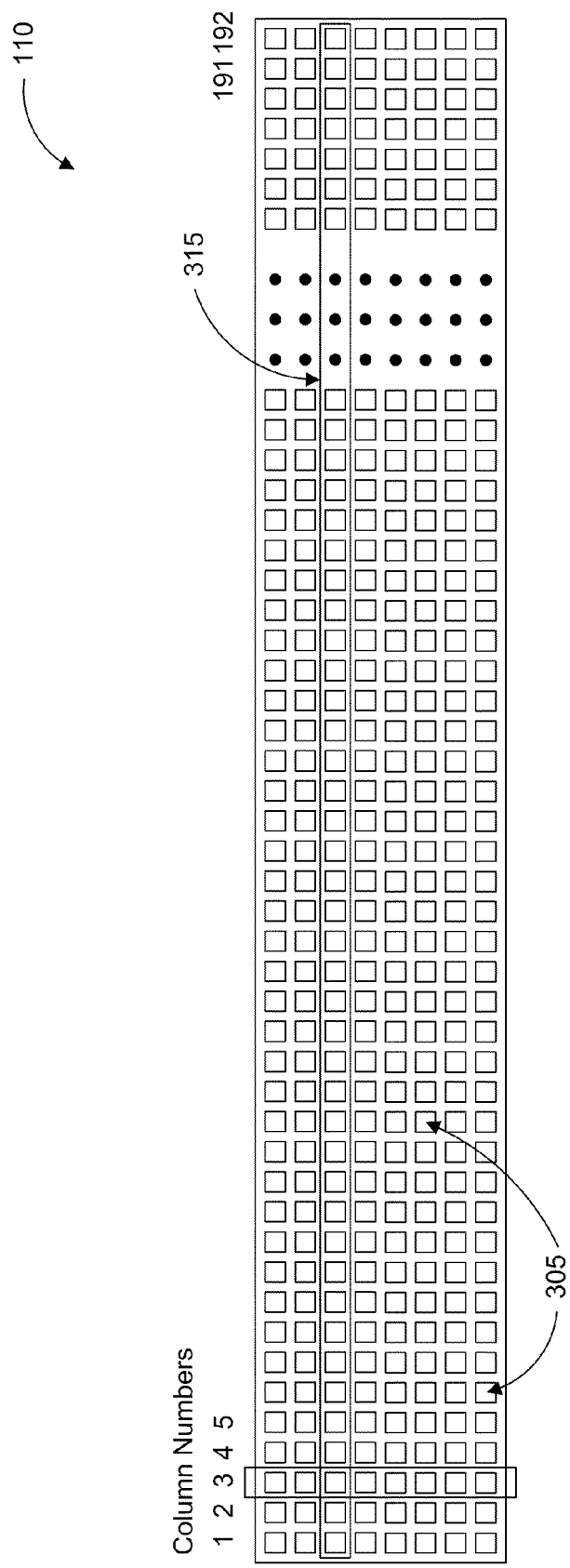
FIG. 3 is an illustration of an exemplary platen of an exemplary fingerprint sensor.

FIG. 3 illustrates a detailed view of exemplary platen 110, which may correspond for example to platen 110 discussed above in conjunction with FIGS. 1A and 1B, platens 110a or 110b discussed above in conjunction with FIGS. 2A and 2B, or to similar platens configured for fingerprint sensing. As discussed above in conjunction with FIGS. 2A and 2B, platen 110 is the fingerprint sensing element of exemplary fingerprint sensors 200a, 200b. Platen 110 is configured to receive a digit of a mammal, such as a person, in order to detect the fingerprint of the person. Additionally, platen 110 is configured to detect a pulse associated with the received digit based upon variations in the fingerprint.

As discussed above, platen 110 may employ a variety of technologies in order to return data descriptive of fingerprint 106. Platen 110 returns data descriptive of fingerprint 106 by detecting the ridges 102 and valleys 104 of fingerprint 106. These detection technologies can, for example, be capacitive, dielectric, optical, thermal, or acoustic. Other technologies can be employed as well. No matter which sensing technology is employed, platen 110 will typically be divided into discrete pixels 305.

Pixels 305 can constitute either discrete physical sensing elements or logical image elements extracted from a fingerprint image or other fingerprint impression. In FIG. 3, each pixel is represented by a small square, while circular black dots provide a representative illustration of a large plurality of pixels (larger than the number of black dots shown) which would too numerous to fit in the space of the illustration.

By way of example, platen 110 can be divided into eight rows 315 of pixels, and 192 columns 310 of pixels 305. In alternative embodiments, different numbers of rows 315 and columns 310 can be employed.

Each pixel 305 is configured to return an image density which is indicative of a presence of a ridge 102 or valley 104 of a fingerprint 106. A pixel 305 fully in contact with a ridge 102 will return a fully darkened color or least magnitude signal, while a pixel 305 in contact with a valley 104 may return fully light, fully white, maximum intensity signal or image intensity. In an alternative embodiment, a pixel 305 in contact with a ridge 102, will return a maximum image intensity while a pixel 305 in contact with a valley 104 may return a minimum image intensity or signal intensity.

A pixel 305 partly in contact with a ridge, and partly in contact with or in proximity to a valley, will return an intermediate value image intensity or signal. Similarly, a pixel 305 which is in contact with a ridge, but where the ridge exerts a less than full pressure on platen 110 will also return an intermediate image intensity or signal intensity.

A pixel 305 is typically configured to return a signal or image intensity in a predetermined range. For example, a pixel 305 can be configured to return an 8-bit value resulting in image intensities ranging from zero to 255 or one to 256. The pattern of image intensities or signal intensities on pixels 305 is used by processing system 225 to identify a fingerprint of a mammal. In addition, and as discussed further below with respect to FIGS. 5 through 8, the pattern of pixels 305 on platen 110 can also be used by processing system 225 to detect the pulse of the mammal.

Exemplary Processing System of a Fingerprint Sensor

Figure 4:
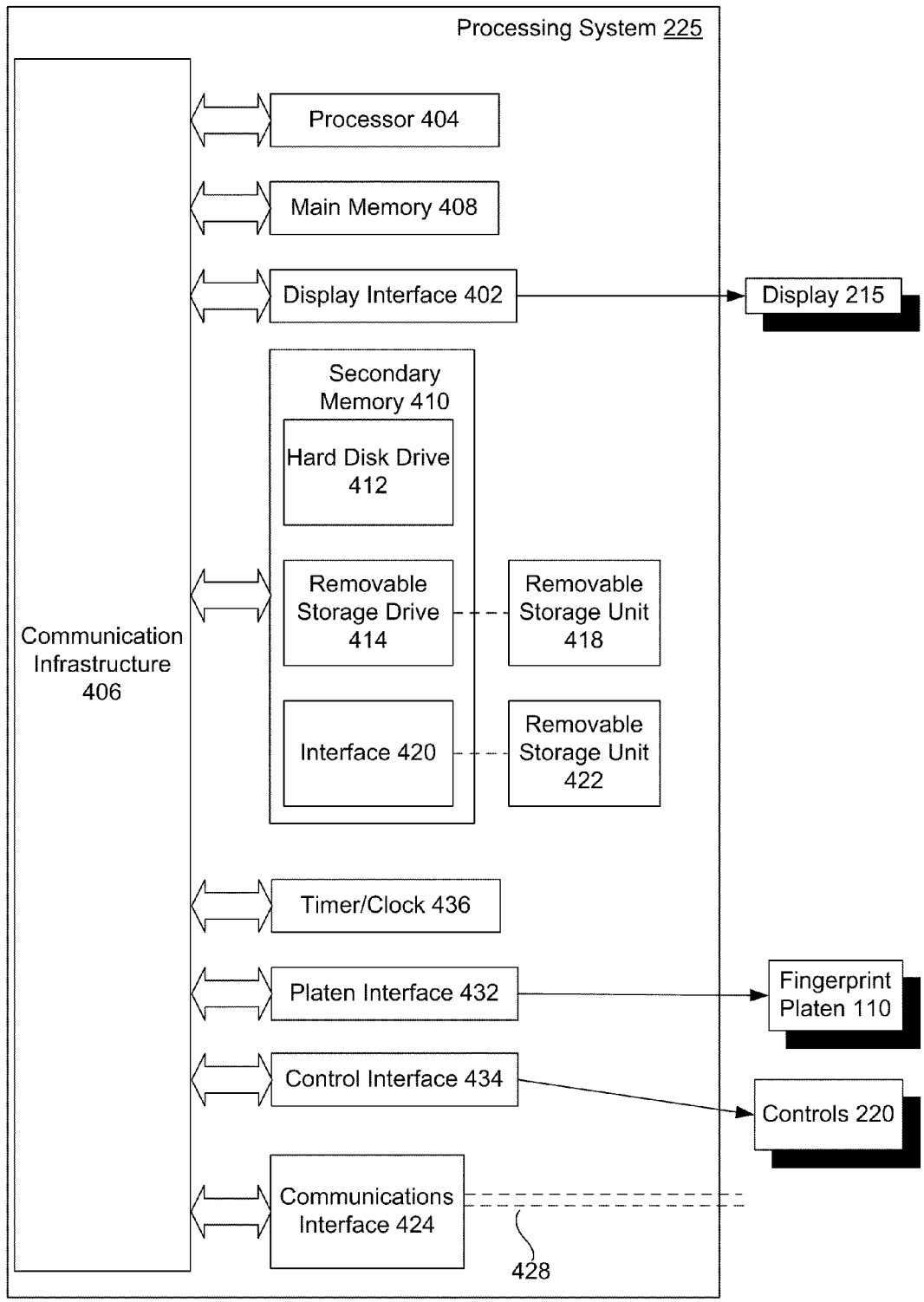
FIG. 4 is a system diagram of an exemplary processing system which is part of an exemplary fingerprint sensor.

In one embodiment, the invention is directed toward one or more processing systems capable of carrying out the functionality described herein. FIG. 4 illustrates an exemplary processing system 225 which can be part of a fingerprint sensor 200. Processing system 225 can be configured, through suitable instructions stored in memory or hard coded into firmware, to detect a fingerprint of a mammal. Processing system 225 may also be configured, through suitable instructions stored in memory or hard coded into firmware, and as described in further detail below, to detect a pulse of a mammal and determine the pulse rate of the mammal. If fingerprint sensor 200 is combined with or integrated into another technology, for example a cell phone, a personal digital assistant, or a computer, processing system 225 may be configured to perform additional processing tasks as well.

Processing system 225 includes one or more processors, which may be a microprocessor, such as processor 404. In an embodiment of the present system and method, processor 404 is configured to detect a variation over time of fingerprint 106, or in a portion of a fingerprint 106, returned by platen 110. In one embodiment of the present system and method, processor 404 is configured to detect the variation over time in fingerprint 106 by comparing images or other fingerprint-descriptive data from a time series of images, or time series of descriptive data, returned by platen 110.

Processor 404 is connected to a communication infrastructure 406 (e.g., a communications bus, cross over bar, or network). The algorithms described herein for detecting a pulse are typically implemented in various software embodiments, which may be executed by exemplary processing system 225 using processor 404. After reading this description, it will become apparent to a person skilled in the relevant art(s) how to implement the invention using other processing systems and/or architectures.

Processing system 225 can include a display interface 402 that forwards graphics, text, and other data from the communication infrastructure 406 (or from a frame buffer not shown) for display on the display unit 215.

Processing system 225 can include a platen interface 432 that receives biometric data and possibly other data from fingerprint platen 110, and that may also be configured to send configuration or control data to fingerprint platen 110.

Processing system 225 can include a control interface 434 that receives control data and control instructions from fingerprint sensor controls 220, and which may also send data to controls 220 (for example, state controls, status display signals, etc.).

Processing system 225 can include timer/clock element 436. Timer/clock element 436 may be configured to maintain a current system date and time, and may also be configured to determine or report the time interval between two or more designated events. Timer/clock element 436 may also be configured for related timing determinations, such as determination of frequencies of designated events. In an embodiment, timer/clock 436 may be a separate element from processor 404. In an alternative embodiment, timer/clock may be integrated into processor 404. In an alternative embodiment, timer/clock 436 may be an external element which delivers a clock signal and timing signals or timing data to processing system 225, for example via communications interface 424 or another interface. In an alternative embodiment, timer/clock 436 may be part of processing system 225, but may be supplemented by external synchronization or timing data.

Processing system 225 also includes a main memory 408, preferably random access memory (RAM), and may also include a secondary memory 410. The secondary memory 410 may include, for example, a hard disk drive 412 and/or a removable storage drive 414, representing a floppy disk drive, a magnetic tape drive, an optical disk drive (CD/DVD/BlueRay drive), USB slot, etc. The removable storage drive 414 reads from and/or writes to a removable storage unit 418 in a well known manner. Removable storage unit 418 represents a floppy disk, magnetic tape, optical disk (CD/DVD/BlueRay, etc.), flash drive, etc. which is read by and written to by removable storage drive 414. As will be appreciated, the removable storage unit 418 includes a computer usable storage medium having stored therein computer software and/or data.

In alternative embodiments, secondary memory 410 may include other similar devices for allowing computer programs or other instructions to be loaded into processing system 225. Such devices may include, for example, a removable storage unit 422 and an interface 420. Examples of such may include a program cartridge and cartridge interface (such as that found in video game devices), a removable memory chip (such as an erasable programmable read only memory (EPROM), or programmable read only memory (PROM)) and associated socket, and other removable storage units 422 and interfaces 420, which allow software and data to be transferred from the removable storage unit 422 to processing system 225.

Processing system 225 may also include a communications interface 424. Communications interface 424 allows software and data to be transferred between processing system 225 and external devices. Examples of communications interface 424 may include a modem, a network interface (such as an Ethernet card), a communications port, a Personal Computer Memory Card International Association (PCMCIA) slot and card, etc. Software and data transferred via communications interface 424 are in the form of signals 428 which may be electronic, electromagnetic, optical or other signals capable of being received by communications interface 424. These signals 428 are provided to communications interface 424 via a communications path (e.g., channel) not shown. This channel carries signals 428 and may be implemented using wire or cable, fiber optics, a telephone line, a cellular link, an radio frequency (RF) link and other communications channels.

In this document, the terms "computer readable physical program medium," "computer usable physical storage medium," "computer readable physical storage medium," and similar terms are used to generally refer to media such as a hard disk installed in hard disk drive 412, removable storage drive 414, interface 420, and the physical removable storage media 418, 422 such as CDs, DVDs, tape drives, flash memory, program cartridge, PCMCIA card, and similar physical media which may be inserted or installed into storage drive 414 or connected or coupled to interface 420. These physical computer program products provide software to processing system 225. The invention is directed in part to such computer program products.

Computer programs (also referred to as computer control logic) are stored in main memory 408 and/or secondary memory 410. Computer programs may also be received via communications interface 424. Such computer programs, when executed, enable the processing system 225 to perform the features of the present invention, as discussed herein. In particular, the computer programs, when executed, enable the processor 404 to perform the features of the present invention directed towards detecting a pulse of a mammal and related functions. Accordingly, such computer programs represent controllers of the processing system 225.

In an embodiment where the invention is implemented using software, the software may be stored in a computer program product and loaded into processing system 225 using removable storage drive 414, hard drive 412, interface 420, removable storage units 418, 422, or communications interface 424. The control logic (software), when executed by the processor 404, causes the processor 404 to perform the functions of the invention to detect a pulse of a mammal and related functions as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

Figure 5A:
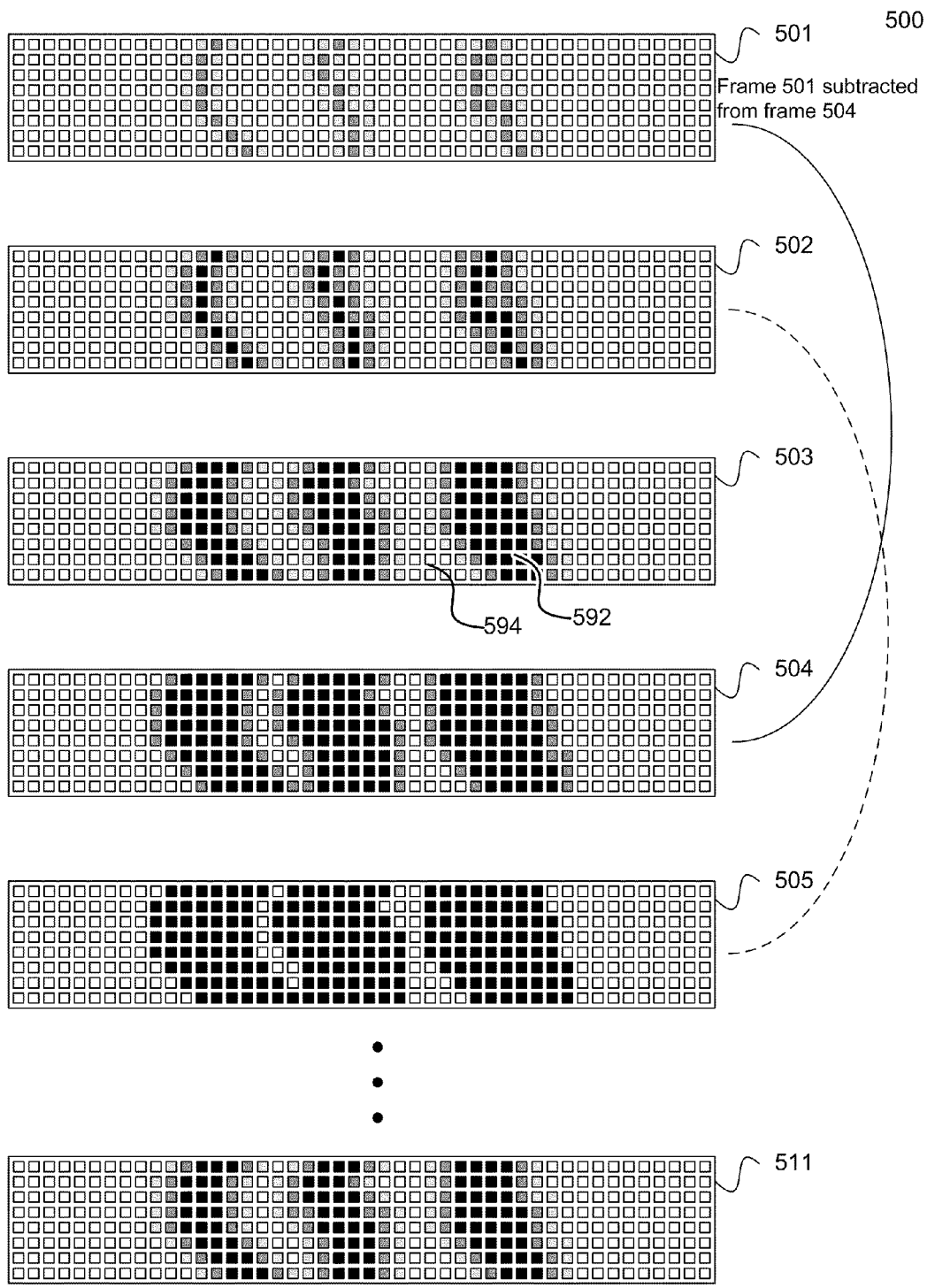
FIG. 5A illustrates an exemplary time series of images of a fingerprint or a portion of a fingerprint as captured by an exemplary platen of an exemplary fingerprint sensor.

In yet another embodiment, the invention is implemented using a combination of both hardware and software.
Exemplary Methods for Detecting a Pulse FIG. 5A is an exemplary series of images 500 from a sensor platen 110 of fingerprint sensor 200. The series of images 500 is a time series of images of a fingerprint 106. In an embodiment, the images are taken at a frame rate of 20 slices per second or 20 frames per second, that is, once every 50 milliseconds.

Through experimentation, a frame rate of approximately 20 slices per second, or 20 frames per second, has been found to be an effective rate for detecting pulse-induced variations in the fingerprint image. At the same time, a frame rate of 20 frames per second is sufficient to enable detection of gross movement or bulk movement of a person's finger, which interferes with the pulse detection process, as discussed further below.

It is noted here that a frame rate of 20 slices per second is, approximately, the lowest or slowest frame acquisition rate that will produce reliable results for detecting a pulse. An advantage of embodiments employing this lowest frame rate of approximately 20 slices per second (or equivalently, twenty frames per second) is that it requires less processing and few frame buffers than higher frame rates. Especially for portable devices, where power and memory may be limited, the conservation of power and memory may be advantageous.

However, in alternative embodiments higher frame rates can be used. Persons skilled in the relevant arts will recognize that the system and method described below may be employed with higher frame rates, provided suitable adjustments are made to the frame-subtraction process and pulse-rate-waveform-array (both described in further detail below). For example, for non-compact, non-portable systems, a frame rate of 100 slices per second might be preferred.

Embodiments described immediately below are based on an exemplary frame rate of 20 slices per second, it being understood that the system and method may be suitably adapted for higher frame rates.

Series of images 500 is a series over eleven consecutive time slices of a fingerprint, numbered 501 through 511, with some time slices (506 through 510) deliberately omitted. It can be seen in successive images, starting from 501 to 502, 502 to 503, and so forth, that as a result of variations in the blood pressure in a person's finger, the image of the fingerprint varies from frame to frame. Image areas corresponding to ridges and valleys have been labeled as 592 (ridges) and 594 (valleys). (It will be appreciated that reference numbers 592 and 594 therefore do not refer to time slices.) It will be further appreciated that slices 501 is representative of a fingerprint image at or near diastole, and slice 505 is representative of a fingerprint image at or near systole. Slice 511 is representative of a fingerprint image during a period of pressure transition marking a return from systole to diastole.

Location variations and/or intensity variations are cyclical in nature, with the cycle corresponding to the pulse rate. So, for example, in series 500, it can be seen that slice 511 corresponds to a period of return to diastole following systole.

It will be understood that time series 500 is representative only, and may not conform in all respects to an actual image of a fingerprint or section of a fingerprint. For example, the number of ridges shown and the spacing between ridges is intended for purposes of illustration only, and may vary from that of a real fingerprint. Similarly, in the time series of images 500 shown in FIG. 5, the variation in ridges 102/592 and valleys 104/594 over time, due to blood pressure changes, has been exaggerated for purposes of illustration.

It may be seen that from slice to slice, the fingerprint image can vary both in the location of a ridge 102 (as shown by the location of ridge images 512), or valley 104 (as shown by the location of valley images 514). The image can also vary in the intensity of a pixel 305 under a ridge 102. Both location variations and intensity variations are induced by the changes in the blood pressure as a result of the pulse. In an embodiment of the present invention, and as discussed in further detail below, the first four images are received into a frame buffer which may for example be stored in memory 408.

By way of example, beginning with a fourth image (e.g., image 504), the third preceding image in the buffer (i.e., three frames back) is subtracted from the present image. In this way, variations in the fingerprint image over time are detected. For example, from frame 504, frame 501 would be subtracted. From frame 505, frame 502 would be subtracted. And from frame 506, frame 503 would be subtracted.

In alternative embodiments, the number of images received into the frame buffer, and the interval between the first frame and second frame (where the first frame is subtracted from the second, later frame) can vary, for example, five frames, six frames, etc. In alternative embodiments with higher frame rates (for example, 100 frames per second), the interval between the first frame and the second frame may be greater still, for example, 10 frames or 20 frames, or some other number as may be determined through testing.

Figure 5B:
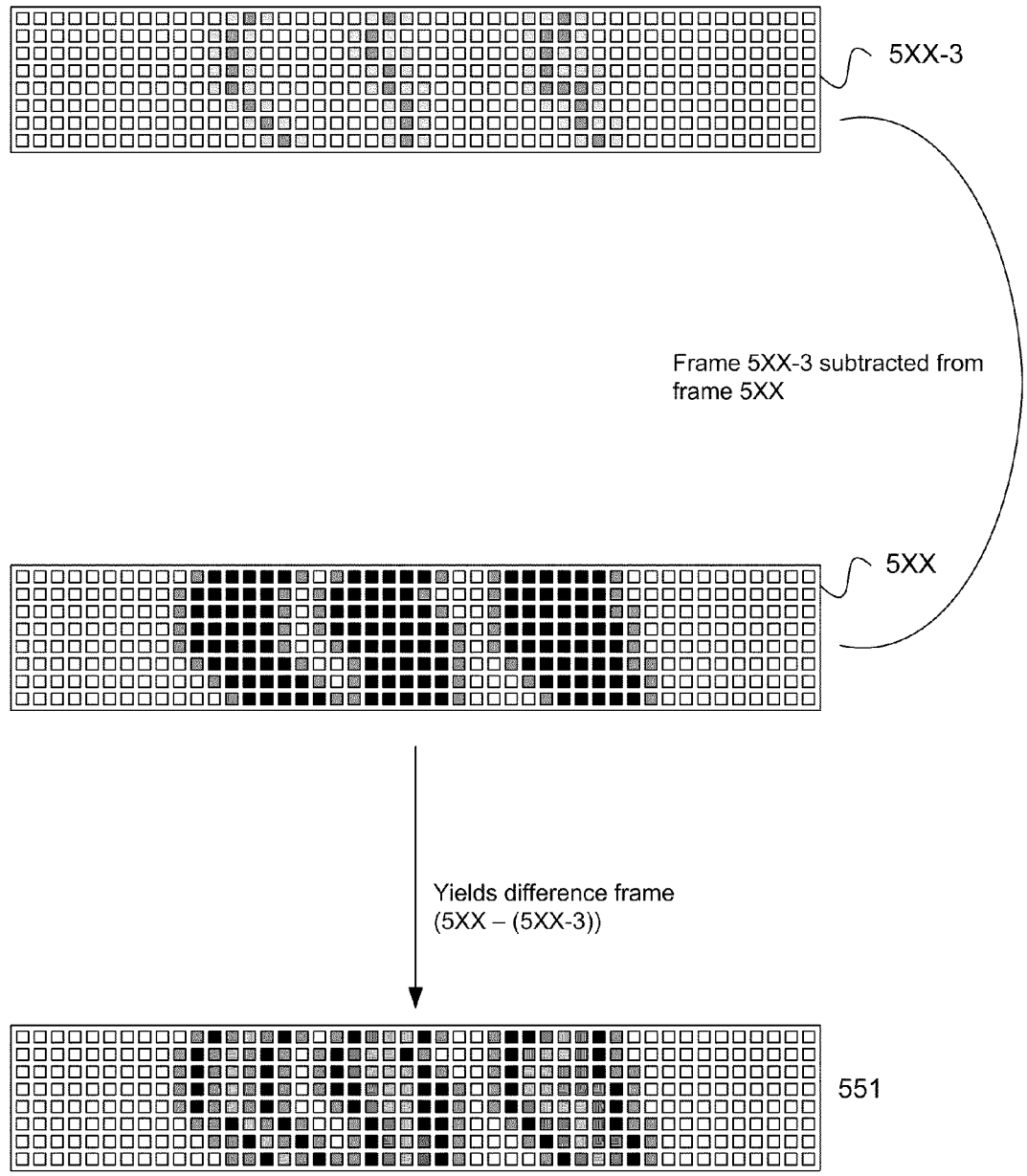
FIG. 5B illustrates subtracting a first, earlier fingerprint image frame from a second, later fingerprint image frame to create a difference frame.

As shown in FIG. 5B, subtraction of a first frame from a second frame entails subtracting, on a basis of corresponding pixels, the pixel value of a first frame from the pixel value of a second frame. Frame 5XX refers to an image from a generic time slice (at some frame count XX), and frame 5XX–N refers to an image from a time slice N frames earlier. For example, 5XX–3 refers to an image slice or image frame 3 frames earlier than frame 5XX.

Regarding image subtraction, for two different frames or image slices (for example, frame 5XX and frame 5XX–3), and for a selected pixel (for example, the upper-left-most pixel), the pixel value of frame 5XX–3 is subtracted from the pixel value of frame 5XX. The resulting difference is stored in a difference frame 551 in memory. This process would be repeated for each pixel, subtracting the pixel value of frame 5XX–3 (the earlier frame) from the pixel value of frame 5XX. A complete difference frame 551 represents the difference between a first frame 5XX–3 and a second, later frame, 5XX.

Only one difference frame is illustrated in FIG. 5B. However, and as discussed in further detail below, embodiments of the present invention entail determining a time series of such difference frames 551, and then comparing the difference frames to determine a pulse rate. Each difference frame in the time series is determined based on a difference between a current frame, represented symbolically as 5XX, and a frame several frames earlier, for example frame 5XX–3.

As discussed above, processing system 225, and processor 404 in particular, are configured to detect a variation over time of fingerprint 106, or in a portion of a fingerprint 106, returned by platen 110.

In particular, processing system 225 is configured to detect the variation over time in fingerprint 106 by comparing fingerprint-descriptive data from a time series of fingerprint descriptive data returned by platen 110. By comparing descriptive data from discrete time slices of the time series, processing system 225 generates a series of data values which are descriptive of fluctuations in fingerprint 106 over time. This series of data values, which represent fluctuations in fingerprint 106 over time, are further analyzed by processing system 225 to determine the pulse of a person or other mammal associated with fingerprint 106.

Figure 6:
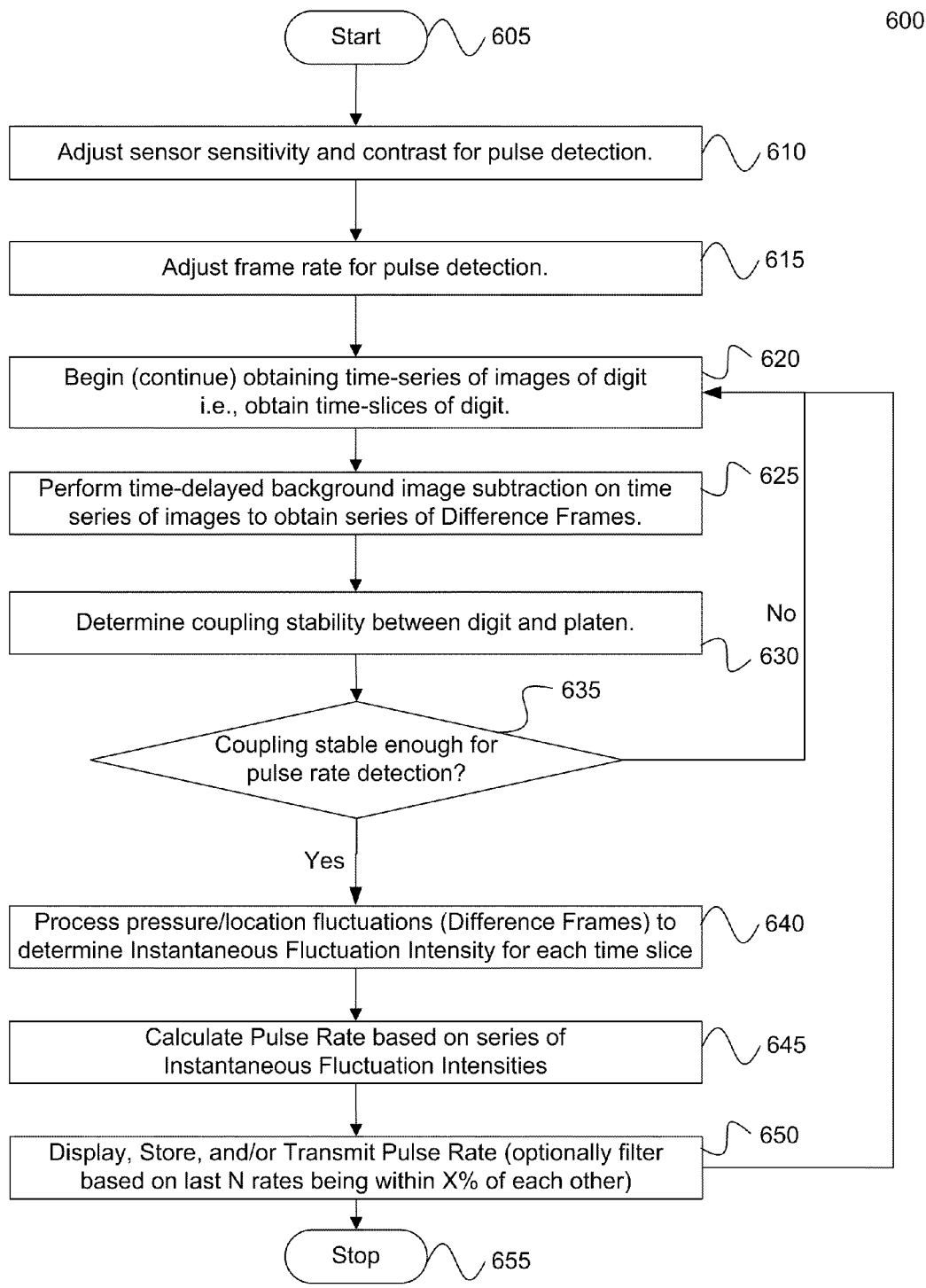
FIG. 6 is a flowchart of an exemplary method of detecting a pulse with a fingerprint sensor.
Figure 7:
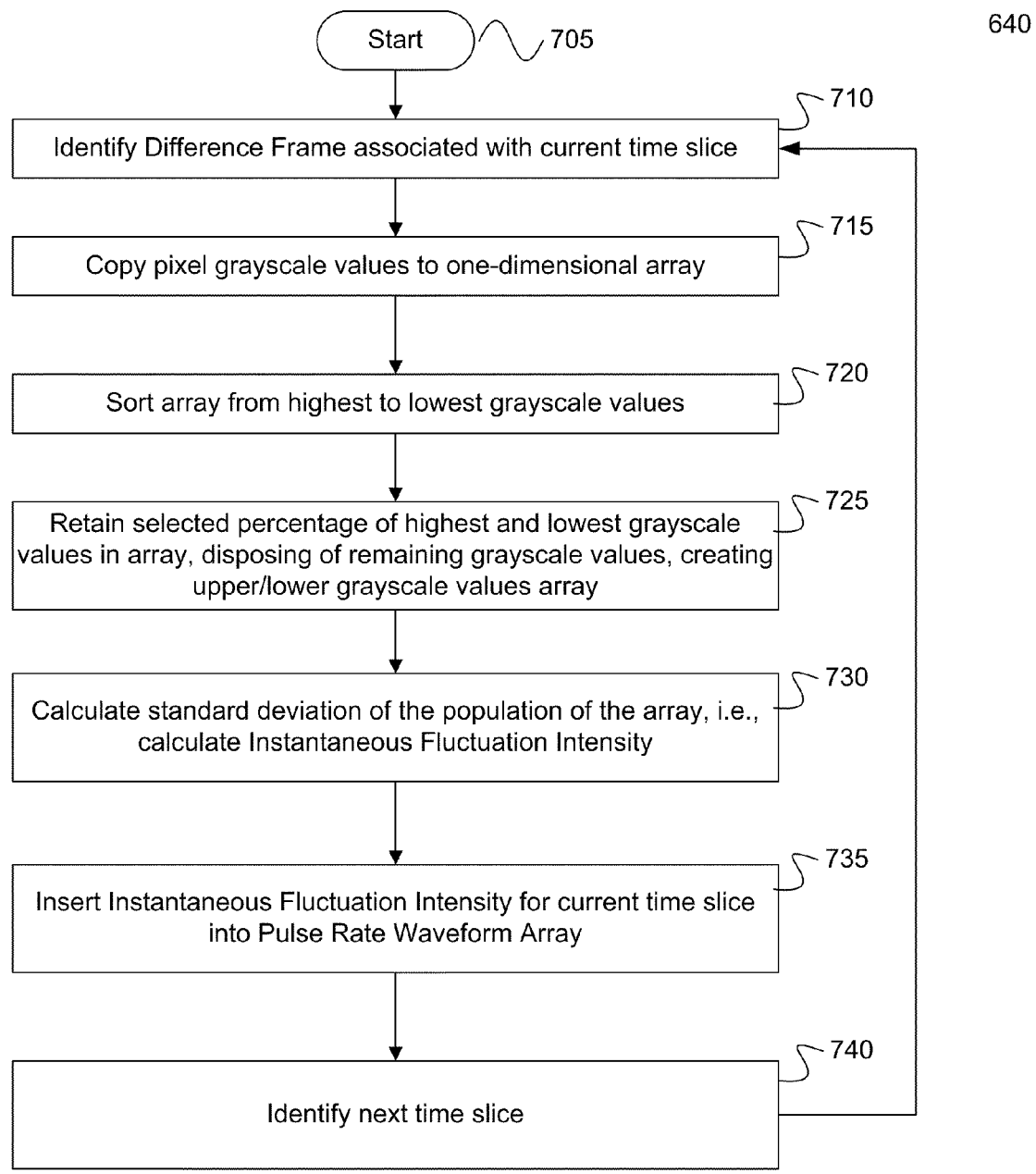
FIG. 7 is a detailed flowchart of one of the steps from the exemplary method of the flowchart of FIG. 6, specifically, a flowchart of an exemplary method to process fluctuations in a fingerprint to determine an instantaneous fluctuation intensity.
Figure 8:
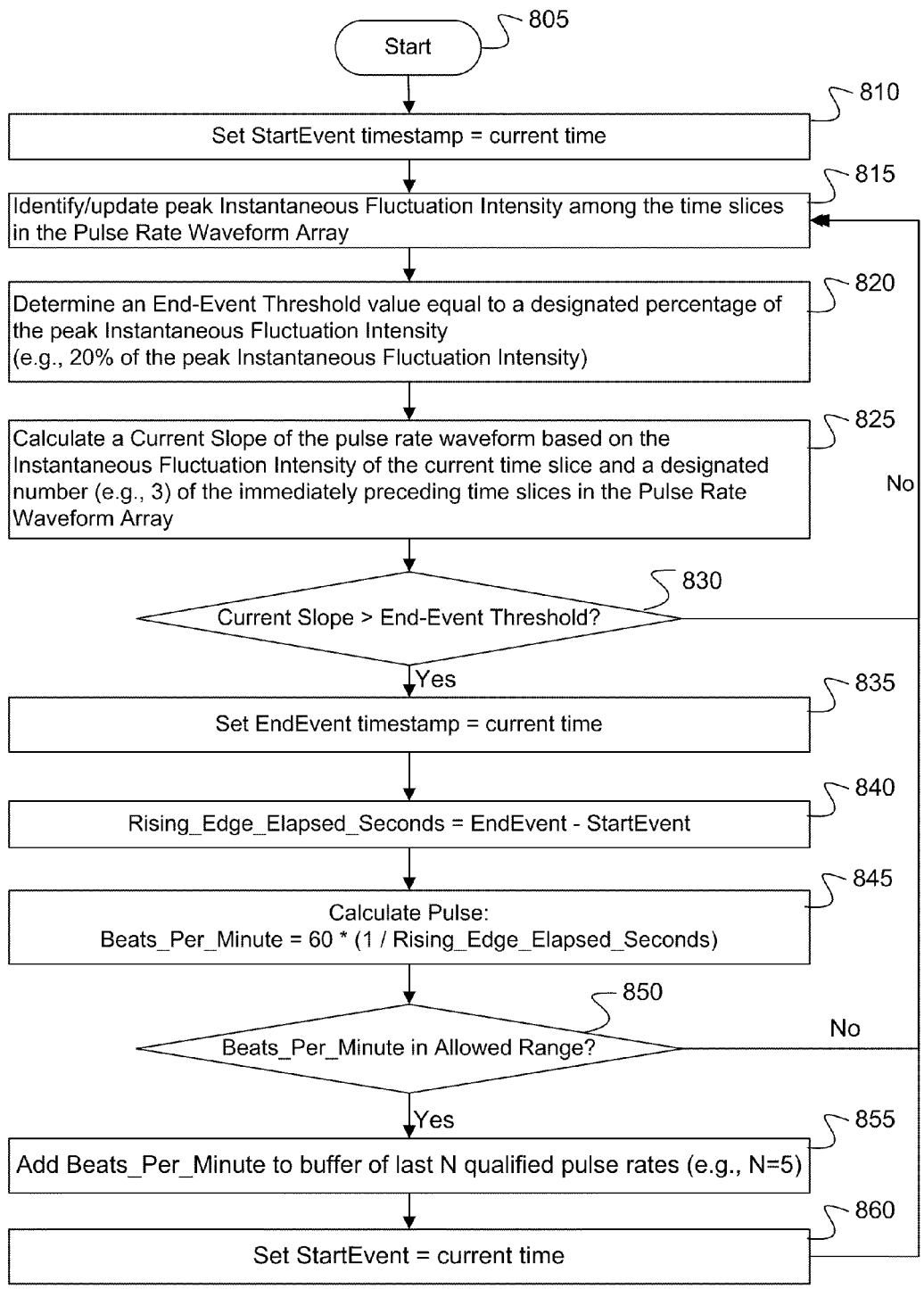
FIG. 8 is a detailed flowchart of one of the steps from the exemplary method of the flowchart of FIG. 6, specifically a flowchart of an exemplary method to calculate a pulse rate based on a time series of instantaneous fluctuation intensities.

In an exemplary embodiment of the present system and method, described in detail in FIGS. 6, 7, and 8, the fingerprint descriptive data obtained from platen 110 is image data 5XX of fingerprint 106. By comparing successive images 5XX, a series of values are generated which are descriptive of differences between the images 5XX. The values are referred to as "instantaneous fluctuation intensities." Further analysis of the series of instantaneous fluctuation intensities yields the pulse.

FIG. 6 is a flowchart of an exemplary method 600 for detecting a pulse with a fingerprint sensor. The method 600 begins at step 605.

At step 610, the sensor is adjusted for image sensitivity and contrast, which is optimized for pulse detection. Typically, for example, the sensor circuitry is adjusted so that the background image corresponding to regions of air (valleys 104) is represented as white (valley images 594). For example, for an eight-bit sensor, the background image is adjusted to have a grayscale value of 255. The circuitry is also adjusted for high sensitivity and high contrast so that the image is approximately 20% binarized, meaning that approximately 20% of the fingerprint image is either completely white or completely black. This maximizes the sensitivity, but leaves enough grayscale content so that pressure fluctuations can be measured.

Put another way, the sensor is adjusted to have a partially saturated image so that valleys 104 appear white and ridges 102 appear black.

In step 615, the frame rate is adjusted for pulse detection. Typically, the sensor 200 is capable of a frame rate greater than 20 frames per second. As indicated above, in one exemplary embodiment a frame rate of 20 slices per second is sufficient to detect a pulse. In alternative embodiments, a frame rate greater than 20 slices per second may be employed. Theoretically, the only upper limit to the sensor frame rate is imposed by (i) The memory required for a large array of frame buffers required to create a high pass filter for every sensor pixel, with a recovery time of approximately 0.2 seconds, and (ii) the processing power required to calculate the instantaneous fluctuation intensities, for each frame, at a given frame rate.

The embodiment described here is based on a frame rate of 20 frames per second, but this is exemplary only, and higher frame rates may be employed. In an embodiment, if sensor noise becomes an issue at the 20 frame per second frame rate, then the frame rate can be doubled and frame averaging can be used to reduce the noise as an element of the signal processing.

Step 620 entails obtaining a time series of images of a digit, that is, obtaining a time series of slices of a fingerprint. The process either begins at step 20 or, if the process is continuing, it continues at step 620. An exemplary time series of fingerprint images 500 is discussed above in conjunction with FIGS. 5A and 5B.

In step 625, time delayed background image subtraction is done on the time series of images. As indicated above (see discussion of FIGS. 5A and 5B), this time delayed image subtraction is typically performed by subtracting from each frame the frame which preceded it by three frames earlier. Thus, the fourth frame would have subtracted from it the first frame, the fifth frame would have subtracted the second frame, the sixth frame would have subtracted from it the third frame. The resulting series of images, which are a series of difference frames 551, are stored in a difference frame buffer, for example in memory 408, for further processing.

An optional step, not shown in the figures, entails a normalization of the difference. For example, if a pixel has a same value in a later time slice than an earlier time slice, rather than the difference pixel value being zero, the difference value for that pixel may be normalized to an intermediate value (for example, 140 on a scale from 0 to 255). With a 0-normalization to 140, a positive difference (that is, a positive result of subtracting the earlier pixel from the later pixel) will result in a difference pixel value in a range from 141 to 255. Similarly, with a 0-normalization to 140, a negative difference (that is, a negative result of subtracting the earlier pixel from the later pixel) will result in a difference pixel value in a range from 0 to 139. Persons skilled in the art will recognize that other 0-normalization values (e.g., other than 140) may be employed as well.

It should be noted that if there were no change at all in the fingerprint over time, the result of subtracting an earlier slice from a later slice would be an entirely uniform difference frame 551. Because the pulse causes variation in the fingerprint over time, the result of the subtraction is a non-uniform difference frame 551, which indicates the difference between the later frame 5XX and the earlier frame 5XX–3.

In step 630, a determination is made based on the series of difference frames 551 as to the coupling stability between the digit of the mammal, or the finger of the mammal, and the platen 110. The details of step 630 are discussed in further detail below. However, the method requires that the mammalian digit in bulk, that is, the digit taken as a whole, be substantially stable and not in motion, that is, that the digit be substantially static in relation to platen 110. While there will be movement of individual ridges 102 and valleys 104, the digit taken as a whole needs to be in a substantially fixed position in relation to platen 110. Therefore, in step 630, the coupling stability between the digit and the platen is determined.

In step 635, a decision is made as to whether the coupling is stable enough for pulse rate detection. If not (that is, the digit is in bulk movement in relation to the platen), pulse rate detection ceases and the method returns to step 620 of obtaining a time series of images of the digit. If in step 635, it is determined that the coupling between the digit and the platen 110 is sufficiently stable for pulse rate detection (that is, the digit in bulk is stationary in relation to the platen), then the method continues at step 640.

In step 640, signal processing is undertaken to process the pressure and/or location fluctuations from one difference frame 551 to the next difference frame 551, to determine instantaneous fluctuation intensity for each time slice. This method of determining instantaneous fluctuation intensity for each time slice is discussed in further detail below in conjunction with FIG. 7.

Following step 640, the method continues with step 645. In step 645, a calculation of the pulse rate is made based on the series of instantaneous fluctuation intensities. Step 645 is discussed in further detail below, in conjunction with FIG. 8. In brief, however, a variation of the instantaneous fluctuation intensities is monitored to determine a cyclic pattern in the instantaneous fluctuation intensities over the time series of slices. Based on the pattern of repetition of instantaneous fluctuation intensities, the pulse is determined.

Step 645 continues with step 650, which entails displaying, storing, and/or transmitting the pulse rate data. Step 650 either continues with step 620, which is obtaining further time series of images of digits, or step 650 continues with step 655, which entails stopping the method.

It will be understood by persons skilled in the relevant arts that the steps shown as part of method 600 in FIG. 6 are exemplary only. Additional steps may be employed and some steps may be optional. For example, adjusting sensor sensitivity and contrast and/or adjusting frame rate may be optional steps. In addition, it will be understood that while the steps are shown in a particular order, and occurring sequentially, that the order of some steps may be changed, and in addition, some steps may occur in parallel through parallel processing.

FIG. 7 is a flowchart of an exemplary method 640 to process pressure/location fluctuations in a fingerprint 106 to determine instantaneous fluctuation intensity for each time slice. FIG. 6 (above) provided an exemplary method 600 for determining a pulse with a fingerprint sensor 200. In particular, in step 625 of method 600, a time delayed background image subtraction was performed to obtain a difference frame 551, and by repeating step 625, a series of difference frames 551 is obtained. In step 640 of method 600, the difference frames 551 are analyzed to determine a numerical value, known as the "instantaneous fluctuation intensity," for each time slice. FIG. 7 presents in detail the method of step 640.

The method 640 begins at step 705.

At step 710 the difference frame 551 associated with the current time slice (that is, associated with the current frame) is identified.

In step 715, the pixel grayscale values from the current difference frame 551 are copied to a one dimensional array in memory 408, which may be a temporary array for storage and processing purposes. In an alternative embodiment, the pixel values may be copied to a long-term storage, for example hard drive 412 or other long-term storage. The exact order in which the pixels are copied from the current difference frame 551 to the temporary one-dimensional storage array does not matter.

After the pixel grayscale values are copied, step 720 follows. In step 720, the array of pixel values is sorted from highest to lowest grayscale values. The sorted values may be stored in the same array, overwriting the unsorted values, or may be stored in separate array storage.

In step 725, the midrange of the grayscale values are deleted from the sorted array. What is retained in the sorted array is a selected percentage of highest and lowest grayscale values in the array. This creates an upper/lower-grayscale-values-array for the difference frame for the current time slice. The values in the upper/lower-grayscale-values-array are the highest pixel values and the lowest pixel values for the current difference frame 551, and so are representative of the difference between fingerprint image for the current time slice, and the fingerprint image for a time slice from several frames earlier.

For example, in an embodiment the retained values in the upper/lower-grayscale-values-array are representative of the difference between the current slice or current fingerprint image, and a slice taken four slices earlier. The highest and lowest grayscale values retained in the upper/lower-grayscale-values-array may as little as two percent of the highest grayscale values and two percent of the lowest grayscale values. In an alternative embodiment, the retained percentage may be as much as ten percent of the highest grayscale values, and ten percent of the lowest grayscale values. Higher percentages may be employed as well.

In step 730 of method 640, a calculation is made as to the standard deviation of the pixel values population of the upper/lower-grayscale-values-array for the current time slice. In other words, the standard deviation of the highest and lowest grayscale values is calculated. Once the standard deviation of the grayscale values is calculated, this standard deviation of the population of the upper/lower-grayscale-values-array is considered to be an "instantaneous fluctuation intensity."

The instantaneous fluctuation intensity is a numerical value embodying or representative of the difference between the fingerprint image of the current slice and the fingerprint image of the preceding time slice that was subtracted from it.

In step 735, the instantaneous fluctuation intensity for the current time slice is inserted into an array structure which is referred to as the "pulse-rate-waveform-array." The pulse-rate-waveform-array stores or maintains a series of consecutive instantaneous fluctuation intensities, representative of a series of changes in the fingerprint 106 over time. The pulse-rate-waveform-array may be stored in main memory 408, hard disk drive 412, or other secondary memory 410.

In step 740 of method 640, the next time slice is identified. The method then continues with step 710, which as noted above identifies the difference frame 551 associated with the current time slice. The method 640 continues in this manner, looping from step 710 through step 740, thus populating the pulse-rate-waveform-array with a time series of instantaneous fluctuation intensities for the fingerprint.

It will be understood by persons skilled in the relevant arts that the steps shown as part of method 640 in FIG. 7 are exemplary only. Additional steps may be employed and some steps may be optional. In addition, it will be understood that while the steps are shown in a particular order, and occurring sequentially, that the order of some steps may be changed, and in addition some steps may occur in parallel through parallel processing.

FIG. 8 is a flowchart of an exemplary method 645 to calculate a pulse rate based upon an array of instantaneous fluctuation intensities. FIG. 6 above included a method step 640 to process pressure/location fluctuations, resulting in difference frames 551 to determine an instantaneous fluctuation intensity for each time slice. Step 640, discussed in greater detail in FIG. 7, yielded a pulse-rate-waveform-array containing a series of instantaneous fluctuation intensities 551. Step 645 entails calculating the pulse rate based on the pulse-rate-waveform-array. The method 645 of FIG. 8 provides further detailed steps to calculate pulse rate according to an exemplary method.

Method 645 starts with step 805.

In step 810, a start-event-timestamp is set which corresponds to the current time. This time information and other timestamp information required by the method 645 can be obtained from timer clock 436 of processing system 225, already discussed above in conjunction with FIG. 4.

Step 815 follows step 810. In step 815, the pulse-rate-waveform-array is surveyed to identify, or if necessary update, a maximum value from among all the instantaneous fluctuation intensity values for all the time slices.

In step 820, an end-event-threshold-value is calculated. The end-event-threshold-value is equal to a designated percentage of the peak instantaneous fluctuation intensity identified in step 815. For example, in an embodiment the end-event-threshold-value may be equal to 20% of the maximum instantaneous fluctuation intensity identified in step 815. In an alternative embodiment, some percentage other than 20% may be employed, for example, 10%.

In step 825, a calculation is made of the current slope of the pulse-rate-waveform (where the pulse-rate-waveform is a graph or plot resulting from plotting the values in the pulse-rate-waveform-array). The current slope is calculated based on the instantaneous fluctuation intensity in the pulse-rate-waveform-array for the current time slice, and a designated number of the immediately preceding time slices in the pulse-rate-waveform-array. For example, the current time slice and the three preceding time slices may be used to determine the current slope of the pulse-rate-waveform. In an alternative embodiment, some other number, for example 4, 5, 10 or other values, may be used for the total number of time slices preceding the current time slice, which are used to calculate the current slope. Whatever number of slices are selected, a current slope is calculated for the pulse-rate-waveform-array.

In step 830, a determination as to whether or not the current slope is greater than the end-event-threshold-value. If not (meaning the current slope is not greater than the end-event-threshold), then the method returns to step 815, which identifies or updates a new peak instantaneous fluctuation intensity among the time slices.

If in step 830, the current slope of the pulse-rate-waveform is greater than the current value of the end-event-threshold, the method continues with step 835, where an end-event-timestamp is set equal to the current time.

In step 840, following step 835, a time interval is identified based on the difference between the end-event-timestamp and the currently set start-event-timestamp. This time difference, the end-event-time minus the start-event-time, may be assigned to a variable known as the rising-edge-elapsed-seconds. The rising-edge-elapsed-seconds is indicative of the time between a most recent pulse of the heart and the immediately preceding pulse of the heart.

In step 845, a pulse calculation is made based on the rising-edge-elapsed-seconds. The formula for calculating the pulse is:

beats-per-minute=60*(1/rising-edge-elapsed-seconds)

In step 850, a determination is made as to whether the beats-per-minutes falls within an allowed range. For example, it is known that the human pulse generally falls in a range between 40 beats-per-minutes and, for example, 120 beats-per-minutes, though persons skilled in the relevant art will recognize other upper and lower bounds may be set. If the pulse (beats-per-minute) that is determined in step 845 is determined to fall outside of the allowed beats-per-minutes range, then the method continues with step 815 of identifying or updating the peak instantaneous fluctuation intensity.

If the beats-per-minutes falls within the allowed range, then in step 855 the beats-per-minutes is added to a buffer of the last several qualified pulse rates (for example, the last five qualified pulse rates).

In step 860 a new start-event-timestamp is set equal to the current time. The method then returns to step 815, of identifying or updating the peak instantaneous fluctuation intensity among the time slices.

It will be understood by persons skilled in the relevant arts that the steps shown as part of method 800 in FIG. 8 are exemplary only. Additional steps may be employed and some steps may be optional. In addition, it will be understood that while the steps are shown in a particular order, and occurring sequentially, that the order of some steps may be changed, and in addition, some steps may occur in parallel through parallel processing.

Exemplary Methods for Determining Bulk Finger Movement

As noted above, the present method for detecting a pulse using a fingerprint sensor depends on the digit of the mammal taken as a whole (that is, in bulk) being substantially stationary relative to platen 110.

Presented here is one exemplary method for determining if this digit is in bulk motion relative to platen 110.

As each time slice 5XX is taken, then for platen 110 the sensor's pixel grayscales are averaged, grouped by column 310. The averages are copied into an averaged-columns array. The averaged-columns array represents the grayscale profile across the X-axis of the platen 110.

The averaged-columns array is populated with multiple sequentially averaged column arrays, for multiple time slices. The regression-line of the averaged-columns array is calculated to produce an X-axis slope. If the slope is too far from zero (+/−) then the finger is moving or the coupling between the finger and platen 110 is unstable.

If the regression-line slope is out-of-range, then the current slice image is disqualified and any further processing is disabled until the finger coupling is stabilized.

Additional Detail and Alternative Embodiments

"Plethysmography" is a method of measuring variations in the size of an organ or body part on the basis of the amount of blood passing through or present in the part, while a "plethysmograph" is a device configured to measure variations in the size of an organ or body part on the basis of the amount of blood passing through or present in the part. The exemplary systems disclosed herein may be viewed as plethysmographs, and the exemplary methods disclosed herein may be viewed as methods of plethysmography.

The methods disclosed herein for analyzing fingerprint data may be viewed in part or whole as methods of digital signal processing for determining a pulse based on fingerprint data, and the processing systems disclosed herein may be viewed in part or whole as digital signal processing systems configured for determining the pulse based on fingerprint data.

As discussed above in conjunction with various embodiments, a background image (that is, an older time slices 5XX–N) is constantly captured from a (N+1)-frame delay-buffer (for example, a four frame delay buffer), and subtracted from current fingerprint image 5XX to normalize the current slice image to a midlevel number of grayscales (for example, 140 grayscales). The subtraction yields difference frame 551. If a person or other mammal places a digit on the platen 110, and no bulk movement or blood-pressure-induced fluctuations take place, then after N slice frames (for example, four frames) the difference frame 551 would appear as a uniform field of pixels at the midlevel grayscale (for example, 140 grayscales). An exemplary target grayscale of 140 is selected so that the grayscale deviations are easier to see on the difference frames 551. With an exemplary midlevel grayscale normalization to 140, the typical peak grayscale fluctuation during pulse-rate acquisition is +/−30 grayscales (that is, approximately 110 to 170 grayscales on a scale of 0 to 255).

In exemplary embodiments discussed above, typically 20 time slices may be taken per second. Combined with the background subtraction algorithm already discussed above (for example, step 625 of exemplary method 600), the background subtraction algorithm effectively creates a high pass filter for every sensor pixel, with a recovery time at 0.200 seconds.

This recovery time of 0.200 seconds is relatively short, when compared with pulse rates on the order of beats-per-minute. The relatively short recovery time is indicated due to the quality and stability of the coupling between the mammalian digit and platen 110. If a user takes a deep breath, squirms, or shifts position, then the DC offset of the pressure waveform (and the position of the fluctuation zones on platen 110) will vary. The skin's pulse-rate-induced pressure fluctuations are fast, causing rapid rise-times, so 0.200 seconds is considered a good compromise between over-attenuation of the pulse signal and pulse-rate signal stability.

In embodiments of the present invention disclosed above, a first, earlier fingerprint 106 image 5XX–N is compared to a second, later fingerprint 106 image 5XX to obtain a difference between the two images. (See for example step 625 of method 600.) In the embodiments disclosed above, the comparison is performed by subtracting corresponding pixel values from the first and second fingerprint 106 images.

In an alternative embodiment, mathematical forms of comparison between two image slices 5XX, 5XX–N other than an operation of subtraction may be used to determine a representative difference value between two time slices or frames of the fingerprint 106. In an alternative embodiment, mathematical forms of comparison between two image slices 5XX, 5XX–N may include subtraction of pixel values, but not necessarily subtraction between corresponding pixels of the first frame and second frame. In an alternative embodiment, mathematical forms of comparison between two image slices 5XX, 5XX–N may include subtraction of pixel values, but may also include additional operations beyond subtraction to determine the representative difference value between two time slices or frames of the fingerprint 106.

In an alternative embodiment, multiple calculations may be employed to determine more than one value or a plurality of values, each different calculated value being indicative in a different way of the difference between a give first time slice and a given second time slice.

In an alternative embodiment, platen 110 may be configured to return data descriptive of a fingerprint 106 other than image data of the fingerprint 106. Processing system 225, and processor 404 in particular, may then be configured to determine an alternative difference between time slices of the fingerprint 106 other than a difference between images. Further, processing system 225, and processor 404 in particular, may be configured to determine the pulse of the mammal based on a variation over time in the alternative difference between time slices.

CONCLUSION

While various embodiments of the present invention have been described above, it should be understood that they have been presented by way of example only, and not limitation. It will be understood by those skilled in the relevant art(s) that various changes in form and details may be made therein without departing from the spirit and scope of the invention as defined in the appended claims. Accordingly, the breadth and scope of the present invention should not be limited by any of the above-described exemplary embodiments, but should be defined only in accordance with the following claims and their equivalents.

What is claimed is:

1. A method of biometric sensing comprising: capturing at a biometric sensing element a time series of at least one of ridges or valleys of at least a portion of a fingerprint; receiving at a processor coupled to the biometric sensing element the time series of at least one of ridges or valleys of the at least the portion of the fingerprint; detecting in the time series a variation over time in the at least one of ridges or valleys of the at least the portion of the fingerprint; and determining a pulse of a mammal associated with the fingerprint based on the variation over time.

2. The method of claim 1, wherein; the time series of at least one of ridges or valleys comprises a series of images of the at least the portion of the fingerprint; and detecting the variation over time in the time series comprises comparing a second image in the time series to a first image in the time series, wherein the first image and the second image are from different times in the time series.

3. The method of claim 2, wherein comparing the second image to the first image yields a data value representative of fluctuations in the at least the portion of the fingerprint from the first image to the second image.

4. The method of claim 2, wherein comparing the second image to the first image comprises subtracting the first image from the second image.

5. The method of claim 2, wherein determining based on the variation over time in the time series the pulse of the mammal comprises: comparing a second plurality of images from the time series to a first plurality of images from the time series, wherein each respective image from the second plurality is compared to a respective earlier image from the first plurality; obtaining from the comparing a plurality data values representative of fluctuations in the fingerprint over time; and analyzing the plurality of data values representative of fluctuations to determine the pulse of the mammal.

6. The method of claim 5, wherein determining based on the variation over time the pulse of the mammal comprises determining a peak in the pulse based on the plurality of data values representative of the fluctuations.

7. The method of claim 6, wherein determining based on the variation over time a pulse of the mammal further comprises: calculating a pulse based on a time interval between a first peak in the pulse and a second peak in the pulse.

8. The method of claim 1, wherein: the time series of at least one of ridges or valleys comprises a series of images of the at least the portion of the fingerprint; and capturing at the biometric sensing element the time series of at least one of ridges or valleys of at least a portion of a fingerprint comprises at least one of: setting at the biometric sensing element an image capture sensitivity substantially higher than an image capture sensitivity used for fingerprint identification; and setting at the biometric sensing element an image contrast substantially higher than an image contrast used for fingerprint identification.

9. The method of claim 1, further comprising determining that a digit associated with said at least the portion of the fingerprint is, in bulk aspect, substantially stationary relative to the biometric sensing element.

10. The method of claim 9, wherein: the time series of at least one of ridges or valleys comprises a series of images of the at least the portion of the fingerprint; and determining that the digit of the mammal is, in bulk aspect, substantially stationary relative to the biometric sensing element comprises comparison of at least a first image and a second image from the time series.

11. A biometric sensor, comprising: a biometric sensing element configured to capture a time series of at least one of ridges or valleys of at least a portion of a fingerprint; and a processor coupled to the biometric sensing element, the processor configured to: receive from the biometric sensing element the time series of at least one of ridges or valleys of the at least the portion of the fingerprint; detect in the time series a variation over time in the at least one of ridges or valleys of the at least the portion of the fingerprint; and determine based on the variation over time a pulse of a mammal associated with the fingerprint.

12. The biometric sensor of claim 11, wherein: the biometric sensing element is configured to capture a time series of images of the at least the portion of the fingerprint; and the processor is configured to detect in the time series of images the variation over time by comparing a second image in the time series to a first image in the time series, wherein the first image and the second image are from different times in the time series.

13. The biometric sensor of claim 12, wherein the processor is further configured to compare the second image to the first image to obtain a data value representative of fluctuations in the at least the portion of the fingerprint from the first image to the second image.

14. The biometric sensor of claim 12, wherein the processor is configured to compare the second image to the first image by subtracting the first image from the second image.

15. The biometric sensor of claim 12, wherein the processor is further configured to: compare a second plurality of images from the time series to a first plurality of images from the time series, wherein each respective image from the second plurality is compared to a respective earlier image from the first plurality; obtain from the comparing a plurality data values representative of fluctuations in the fingerprint over time; and analyze the plurality of data values representative of fluctuations to determine the pulse of the mammal.

16. The biometric sensor of claim 15, wherein the processor is further configured to determine a peak in the pulse based on the plurality of data values representative of the fluctuations.

17. The biometric sensor of claim 16, wherein the processor is further configured to calculate a pulse based on a time interval between a first peak in the pulse and a second peak in the pulse.

18. The biometric sensor of claim 11, wherein: the biometric sensing element is configured to capture a time series of images of the at least the portion of the fingerprint; and the biometric sensing element and/or the processor are configured for at least one of: an image capture sensitivity substantially higher than an image capture sensitivity used for fingerprint identification; and an image contrast substantially higher than an image contrast used for fingerprint identification.

19. The biometric sensor of claim 11, wherein the processor is further configured to determine that a digit associated with said at least the portion of the fingerprint is, in bulk aspect, substantially stationary relative to the biometric sensing element.

20. The biometric sensor of claim 19, wherein: the biometric sensing element is configured to capture a time series of images of the at least the portion of the fingerprint; and the processor is configured to determine that the digit of the mammal is, in bulk aspect, substantially stationary relative to the biometric sensing element by comparing at least a first image and a second image from the time series.

21. A non-transitory computer readable medium having control logic stored thereon, the control logic comprising machine executable code which when executed by a processor causes the processor to: receive from a biometric sensing element a time series of at least one of ridges or valleys of at least a portion of a fingerprint; detect in the time series a variation over time in the at least one of ridges or valleys of the at least the portion of the fingerprint; and determine based on the variation over time a pulse of a mammal associated with the fingerprint.

22. The non-transitory computer readable medium of claim 21, further comprising machine executable code which when executed by the processor causes the processor to: receive from the biometric sensing element a time series of images of the at least the portion of the fingerprint; and detect the variation over time in the time series by comparing a second image in the time series to a first image in the time series, wherein the first image and the second image are from different times in the time series.

23. The non-transitory computer readable medium of claim 22, further comprising machine executable code which when executed by the processor causes the processor to: compare the second image to the first image to obtain a data value representative of fluctuations in the at least the portion of the fingerprint from the first image to the second image.

24. The non-transitory computer readable medium of claim 22, further comprising machine executable code which when executed by the processor causes the processor to: compare the second image to the first image by subtracting the first image from the second image.

25. The non-transitory computer readable medium of claim 22, further comprising machine executable code which when executed by the processor causes the processor to: compare a second plurality of images from the time series to a first plurality of images from the time series, wherein each respective image from the second plurality is compared to a respective earlier image from the first plurality; obtain from the comparing a plurality data values representative of fluctuations in the fingerprint over time; and analyze the plurality of data values representative of fluctuations to determine the pulse of the mammal.

26. The non-transitory computer readable medium of claim 25, further comprising machine executable code which when executed by the processor causes the processor to: determine a peak in the pulse based on the plurality of data values representative of the fluctuations.

27. The non-transitory computer readable medium of claim 26, further comprising machine executable code which when executed by the processor causes the processor to: calculate a pulse based on a time interval between a first peak in the pulse and a second peak in the pulse.

28. The non-transitory computer readable medium of claim 21, further comprising machine executable code which when executed by the processor causes the processor to establish in a time series of images of the fingerprint obtained via the biometric sensing element at least one of: an image capture sensitivity substantially higher than an image capture sensitivity used for fingerprint identification; and an image contrast substantially higher than an image contrast used for fingerprint identification.

29. The non-transitory computer readable medium of claim 21, further comprising machine executable code which when executed by the processor causes the processor to: determine that a digit associated with the at least the portion of the fingerprint is, in bulk aspect, substantially stationary relative to the biometric sensing element.

30. The non-transitory computer readable medium of claim 29, further comprising machine executable code which when executed by the processor causes the processor to: determine that the digit of the mammal is, in bulk aspect, substantially stationary relative to the biometric sensing element by comparing at least a first image and a second image from a time series of images of the least the portion of the fingerprint received from the biometric sensing element.

* * * * *